United States Patent
Farnia et al.

(10) Patent No.: US 6,838,573 B1
(45) Date of Patent: Jan. 4, 2005

(54) COPPER CVD PRECURSORS WITH ENHANCED ADHESION PROPERTIES

(75) Inventors: Morteza Farnia, Campbell, CA (US); Robert Sam Zorich, Carlsbad, CA (US); James Richard Thurmond, Temecula, CA (US); John Anthony Thomas Norman, Encinitas, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/768,370

(22) Filed: Jan. 30, 2004

(51) Int. Cl.⁷ .............................. C07F 1/08; C07F 7/08; C23C 16/00
(52) U.S. Cl. .............................. 556/41; 556/12; 556/40; 556/112; 427/587; 427/248.1
(58) Field of Search .............................. 556/12, 40, 41, 556/112; 427/248.1, 587

(56) References Cited

U.S. PATENT DOCUMENTS

| | | | |
|---|---|---|---|
| 5,085,731 A | | 2/1992 | Norman et al. |
| 5,098,516 A | | 3/1992 | Norman et al. |
| 5,187,300 A | | 2/1993 | Norman |
| 5,220,044 A | * | 6/1993 | Baum et al. ............. 556/40 |
| 5,994,571 A | | 11/1999 | Zhuang et al. |
| 6,015,918 A | | 1/2000 | Zhuang et al. |
| 6,090,963 A | * | 7/2000 | Zhuang et al. ........... 556/112 |
| 6,090,964 A | * | 7/2000 | Rhee et al. ............. 556/117 |
| 6,096,913 A | | 8/2000 | Norman et al. |
| 6,130,345 A | * | 10/2000 | Doppelt ............. 556/12 |
| 6,245,261 B1 | * | 6/2001 | Zhuang et al. ............. 252/519.2 |
| 6,281,377 B1 | * | 8/2001 | Zhuang et al. ............. 556/112 |
| 6,534,666 B1 | * | 3/2003 | Zorich et al. ............. 556/41 |
| 6,764,537 B2 | * | 7/2004 | Zhuang et al. ............. 106/1.26 |

FOREIGN PATENT DOCUMENTS

| | | |
|---|---|---|
| EP | 0 630 988 A1 | 12/1994 |
| EP | 0 630 988 B1 | 7/1997 |
| JP | 7215982 A2 | 8/1995 |
| JP | 7252266 A2 | 10/1995 |
| JP | 8053468 A2 | 2/1996 |
| JP | 10140352 | 5/1998 |

OTHER PUBLICATIONS

S.W. Kang, et al, (hfac)(Cu(I)(MP) (hfac=hexafluoroacetylacetonate, . . . , Thin Solid Films 350 (1999) P. 10–13.

* cited by examiner

Primary Examiner—Porfirio Nazario-Gonzalez
(74) Attorney, Agent, or Firm—Geoffrey L. Chase

(57) ABSTRACT

This invention relates to copper(+1)(β-diketonate)(L) and related copper complexes such as copper (+1)(β-ketoiminate)(L) represented by the formula:

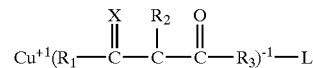

wherein X represents O or $NR_9$, $R_1$ and $R_3$ are each independently comprised of the group $C_{1-8}$ alkyl, $C_{1-8}$ fluoroalkyl, aryl, $C_{1-8}$ alkoxy, and $C_{1-8}$ alkyl ethers and $R_2$ is H, $C_{1-8}$ alkyl, $C_{1-8}$ alkoxy, and halogen, $R_9$ is $C_{1-8}$ alkyl, $C_{1-8}$ fluoroalkyl, phenyl, alkylphenyl, trialkylsilyl, and L represents a ligand having the structure:

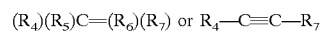

wherein $R_4$, is comprised of the group $C_{1-8}$ alkanol, $C_{1-8}$ alkoxyalkanol, $C_{1-8}$ unsaturated alkoxyalkanol, trialkylsilanol, $C_{1-8}$ aalkylamine, phenylamine; $R_5$, $R_6$, and $R_7$ are comprised of the group H, $C_{1-8}$ alkyl, trialkylsilyl, alkoxy or phenyl.

20 Claims, No Drawings

COPPER CVD PRECURSORS WITH ENHANCED ADHESION PROPERTIES

BACKGROUND OF THE INVENTION

In the electronics industry there is a steady trend towards manufacturing microprocessors and memory devices of increasingly high speed and large information storage capacity. This requires the individual electrical devices such as transistors, etc. within the microprocessors to be fabricated at an increasingly small scale. The metallic electrical interconnects between the devices also need to be miniaturized. As device and interconnect dimensions fall below one-quarter of a micron, the choice of interconnect metal becomes critical.

Chemical vapor deposition of copper metal using fluorinated organometallic copper compounds has been widely used in the electronics industry for the above applications. Specifically, copper metal is deposited on metallic substrates or other electrically conducting portions of a substrate employing CVD methods. The ability of the organo copper complexes to deposit a metallic copper film which has good adhesion to the substrate and produce a copper film having low resistivity are two requirements of the organo copper complexes and the CVD process employed.

One class of organo copper complexes widely used for the deposition of copper films by a CVD process is a copper(+1)(β-diketonate)(L) complex where (L) represents a stabilizing ligand, typically a non-aromatic unsaturated group including silylolefins and silylalkynes. The following patents are representative of copper(+1)(β-diketonate)(L) complex for chemical vapor deposition in the electronics industry.

U.S. Pat. No. 5,085,731 discloses organometallic complexes based upon copper(+1)(β-diketonate)(L) complexes where (L) is a silylolefin stabilizing ligand. These are represented by the formula:

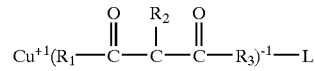

wherein $R_1$ and $R_3$ are each independently $C_1-C_8$ perfluoroalkyl, $R_2$ is H, F or $C_1-C_8$ perfluoroalkyl, $R_4$ is H, $C_1-C_8$ alkyl, or $Si(RN)_3$, each $R_5$ is independently H or $C_1-C_8$ alkyl, and each $R_6$ is independently phenyl or $C_1-C_8$ alkyl. One type of complex is prepared by reacting a copper salt, e.g., copper chloride with the potassium salt of hexafluoroacetylacetone, i.e., $(K^{+1}(hfac)^{-1})$, and a silylolefin in hexane or other solvent.

U.S. Pat. No. 5,187,300 discloses organometallic copper complexes suited for selectively depositing copper films onto electrically conducting portions of a substrate under CVD conditions. These copper complexes are based upon copper(+1)(β-diketonate)(L) where (L) is a silylalkyne stabilizing ligand. This type of complex is prepared by the reaction of the potassium salt of hexafluoroacetylacetone with copper chloride in the presence of a silylalkyne stabilizing ligand. These complexes have the formula:

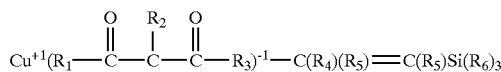

wherein $R_1$ and $R_3$ are each independently $C_1-C_8$ perfluoroalkyl, $R_2$ is H, F or $C_1-C_8$ perfluoroalkyl, $R_4$ is H, $C_1-C_8$ alkyl, phenyl, or $Si(R_5)_3$, and each $R_5$ is independently $CL-C_8$ alkyl or phenyl.

U.S. Pat. No. 5,098,516 discloses organo copper compounds of the formula:

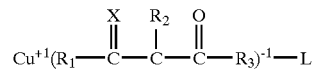

wherein $R_1$ and $R_3$ are each independently $C_1-C_8$ perfluoroalkyl, $R_2$ is H or $C_1-C_8$ perfluoroalkyl and L is carbon monoxide, an isonitrile or an unsaturated hydrocarbon ligand containing at least one non-aromatic unsaturation. These copper(+1)(β-diketonate)(L) compounds are also prepared by the reaction of the potassium salt of hexafluoroacetylacetone with copper chloride in the presence of a stabilizing ligand.

U.S. Pat. No. 6,096,913 discloses the synthesis of copper (+1)(β-diketonate)(L) type complexes by the reaction of a β-diketone with cuprous oxide in the presence of stabilizing ligand (L) and finely divided copper powder to suppress the formation of unwanted copper(+2)bis(hexafluoroacetylacetonate). The process is described by the following equation:

$$2Hhfac + Cu_2O + 2(L) = 2Cu(+1)(hfac)(L) + H_2O$$

BRIEF SUMMARY OF THE INVENTION

This invention relates to copper(+1)(β-diketonate)(L) and related copper complexes such as copper(+1)(β-ketoiminate)(L) According to the present invention, preferred volatile copper complexes are provided and represented as shown:

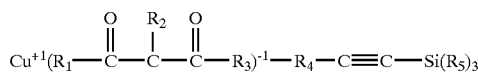

wherein X represents O or $NR_9$, $R_1$ and $R_3$ are each independently comprised of the group $C_{1-8}$ alkyl. $C_{1-8}$ fluoroalkyl, aryl, $C_{1-8}$ alkoxy, and $C_{1-8}$ alkyl ethers and $R_2$ is H, $C_{1-8}$ alkyl, $C_{1-8}$ alkoxy, and halogen, $R_9$ is $C_{1-13}$ alkyl, $C_{1-8}$ fluoroalkyl, phenyl, alkylphenyl, trialkylsilyl, L represents a ligand having the structure

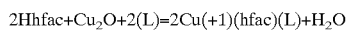

wherein $R_4$ is comprised of the group $C_{1-8}$ alkanol, $C_{1-8}$ alkoxyalkanol, Cue unsaturated alkoxyalkanol, trialkylsilanol, $C_{1-8}$ alkylamine, phenylamine; $R_5$, $R_6$, and $R_7$ are comprised of the group H, $C_{1-8}$ alkyl, triakylsilyl, alkoxy or phenyl.

There are many advantages that may be obtained using the unique copper(+1)(β-diketonate)(L) and copper (+1)(β-ketoiminate)(L) complexes, these include:

- an ability to deposit thin metallic copper films having excellent adhesion to metal surfaces such as Ta, TaN, TaSiN, Ir, Rh, Ru, Pt, Ti, TiN, TiSiN, W, WN, WSiN and to dielectric surfaces;
- an ability to blend the copper(+1)(β-diketonate)(L) or copper(+1)(β-ketoiminate)(L) complexes having hydroxyl functionality with other monovalent β-diketonate or β-ketoiminate copper complexes and thereby tailor the film deposition properties such as deposition rates and temperatures of the resulting mixtures;
- an ability to selectively deposit copper onto metallic or other electrically conducting portions of a substrate surface at temperatures less than 350° C.;

an ability to deposit copper films by means of chemical vapor deposition at low temperature; and, an ability to facilitate reduction of copper(+1)(β-diketonate)(L) complexes to metallic copper at high deposition rates.

DETAILED DESCRIPTION OF THE INVENTION

In the basic process for preparing Cu(+1)(β-diketonate) (L)complexes, sometimes referred to as monovalent copper β-diketone complex products, a reactive copper compound is reacted with the H-form or the K-form of a β-diketone, e.g., the H-form or $K^{+1}$ form of the fluorinated O-diketone, hexafluoroacetylacetone (Hhfac) or ($K^+$hfac$^-$) respectively, in the presence of a stabilizing ligand (L) and in the presence or absence of a solvent. These ligands (L) act to stabilize the copper(+1)β-diketonate(L)complex during vaporization and delivery to the CVD chamber and to the target silicon wafer surface to be metallized. At the heated wafer surface the ligand (L) desorbs to leave behind an unstable copper(+1) (β-diketonate)species which disproportionates to copper metal and the divalent copper β-diketonate complex, i.e., $Cu^{+2}$(β-diketonate)$_2$. In this invention specific copper(+1) (β-diketonate)(L) complexes are described where the olefin or alkyne bears an appended alcohol or amine functionality, which whilst not wishing to be bound by theory, is thought to be capable of donating a hydrogen atom to the CVD reaction, as well as potentially acting as a reductant towards the copper(+1) species.

Specific copper β-diketonate and β-ketoiminate complexes are represented by the following formula:

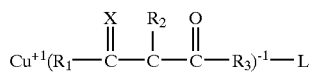

wherein X represents O or $NR_9$ wherein, $R_1$ and $R_3$ are each independently comprised of the group $C_{1-8}$ alkyl, $C_{1-8}$ fluoroalkyl, aryl, $C_{1-8}$ alkoxy, and $C_{1-8}$ alkyl ethers and $R_2$ is H, $C_{1-8}$ alkyl, $C_{1-8}$ alkoxy and halogen, $R_9$ is $C_{1-8}$ alkyl, $C_{1-8}$ fluoroalkyl, phenyl, alkylphenyl, trialkylsilyl, L represents a ligand having the structure

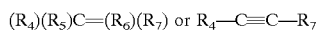

wherein $R_4$ is comprised of the group $C_{1-8}$ alkanol, $C_{1-8}$ alkoxyalkanol, $C_{1-8}$ unsaturated alkoxyalkanol, trialkylsilanol, $C_{1-8}$ alkylamine, phenylamine; $R_5$, $R_6$, and $R_7$ are comprised of the group H, $C_{1-8}$ alkyl, triakylsilyl, alkoxy or phenyl.

In the above, preferred compounds include those where X is O, $R_1$ and $R_3$ are $C_{1-3}$ alkyl, typically fluoroalkyl and most preferably, $CF_3$, $R_2$ is H, $R_4$ is a $C_{1-3}$ alkanol, preferably $(CH_3)_2COH$, $R_5$, $R_6$ and $R_7$ are H where L is olefinic and $R_4$ is $CH_2OH$ and R7 is $C_{1-3}$ alkyl or H when L is alkyne.

Representative reactive copper compounds from which to prepare monovalent copper(+1)(β-diketonate)(L) and copper (+1) (β-ketoiminate)(L) complex product include cuprous oxide, cuprous chloride, cuprous bromide, cuprous acetate and other suitable copper(+1) compounds commonly used to prepare a monovalent copper(+1)(β-diketonate)(L) complex and copper(+1) (β-ketoiminate)(L) products. These new compounds may also be prepared by electrochemical synthesis.

Representative ketones and ketoimines particularly suited for preparing the copper complexes are the fluorinated β-diketones and fluorinated β-ketoimines from which monovalent copper(+1)(β-diketonate) or copper(+1)(β-ketoiminate)(L) complex products can be synthesized. Representative examples include: 1,1,1,5,5,5-hexafluoro-2,4-pentanedione (sometimes referred to herein as hexafluoroacetylacetone); 1,1,1,3,5,5,5-heptafluoro-2-4-pentanedione, 4-(2,2,2-trifluoroethyl)imino-1,1,1,5,5,5-hexafluoro-2-pentanone; 5-(2,2,2-trifluoroethyl)imino-1,1,1,2,2,6,6,6-octafluoro-3-hexanone.

In preferred compounds represented where X is $NR_9$, R is $CH_3$, $R_1=R_3=CF_3$, $R_2=H$, $R_4=CH_2CF_3$ in the ketoimine anion and wherein where the ligand (L) is olefinic $R_4$ is $CH_2COH$ and $R_5$, $R_6$ and $R_7$ is H.

A wide variety of hydroxyl or amine containing olefins and alkynes can be used as the ligands (L) represented in the general formula of (copper)+1(β-diketonate)(L) compounds where X is 0 and the (copper)+1β-ketoiminate)(L) complex shown in the formula where X is $NR_9$ from which copper metallic films of enhanced adhesion and low resistivity may be obtained. These include, but are not limited to 2-methyl-3-buten-2-ol, 3-methyl-2-buten-1-ol, 2-methyl-2-propene-1-ol, 2-methyl-2-buten-1-ol, 4-amino butene, and 2-butyne-1-ol.

Blends of the monovalent copper complexes employing ligands having hydroxyl, amine or other active hydrogen functionality with monovalent complexes employing ligands not having hydroxyl or other hydrogen functionality can be effected in two ways. For example, the ligands of the type (L*) bearing hydroxyl, amine or other active hydrogen functionality can be added to the copper(+1)(β-diketonate) (L) complexes to create copper(+1)(β-ketonate)L* precursors in situ, by the process of Dynamic Ligand Exchange (DLE). In the exchange (L*) effectively competes with (L) for coordinaton to the copper center in copper(+1)(β-diketonate)(L) complexes. This mixture can be directly injected into the vaporizer of a copper CVD chamber. As might be expected, such mixtures of copper(+1)(β-diketonate)(L) complexes and copper(+1)(β-diketonate) (L*) complexes can also be prepared by injecting an olefin or alkyne (L) into the CVD reactor in which, a copper (+1)(β-diketonate)(L*) complex is being utilized or vice versa where an olefin or alkyne (L*) is injected into a CVD reactor running a copper(+1)(β-diketonate)(L) complex. In these ways the desired quantity of the active hydrogen, olefin or alkyne is brought to the CVD reaction. In its simplest manifestation, these mixtures are also obtained by directly mixing compatible precursors that bear (L) and (L*) respectively.

In the preparation of conventional copper(+1)(g-diketonate)(L) complexes for blending, a wide variety of non-hydroxyl or nonorgano amine ligands (L) may be used as the stabilizing ligand. These include: isonitriles olefins such as ethylene, hexadiene, dimethylbutene, dimethyl pentene, cyclooctene, 1,5-cyclooctadiene, cyclooctadecatriene and the like and acetylenics such as isopropylacetylene, diphenylacetylene. Silylolefins and silylacetylenes include trimethylvinylsilane (TMVS) and trimethylsilyl propyne (TMSP). Representative monovalent copper based complexes of a β-diketone for blending are represented by the formulas below:

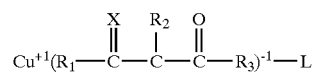

wherein X represents O or $NR_9$ wherein $R_1$ and $R_3$ are each independently comprised of the group $C_{1-8}$ alkyl, $C_{1-8}$ fluoroalkyl, aryl, $C_{1-8}$ alkoxy, and $C_{1-8}$ alkyl ethers and $R_2$ is H or $C_1$–$C_8$ fluoroalkyl, alkyl, alkoxy, halogen. $R_9$ is $C_{1-8}$ alkyl, $C_{1-8}$ fluoroalkyl, phenyl, alkylpheny, trialkylsilyl. In the ligand portion L is carbon monoxide, an isonitrile or an unsaturated hydrocarbon ligand containing at least one non-aromatic unsaturation.

Although not intending to be bound by theory it is thought that enhanced adhesion is effected because these precursors are capable of donating hydrogen from the coordinating ligand (L) to the substrate surface and in doing so help to lessen the deposition of fluorocarbon containing species and thus improve adhesion of copper to the substrate.

The following examples are intended to illustrate various embodiments of the invention.

General Synthesis Procedure

The copper(+1)(β-diketonate)(L) complex products can be synthesized in accordance with the following general procedure:

(a) A reaction vessel equipped with a mechanical stirrer is prepared and purged with $N_2$.

(b) 0.7 moles of $Cu_2O$ and 0.15 moles of powdered Cu are added to the reaction vessel.

(c) Then 1.85 moles of ligand (L) or (L*) is placed into the reaction vessel and the mixture stirred vigorously to ensure a thorough wetting of the powders.

(d) The vessel is then placed into a water bath and cooled to 12° C.

(e) At this time 1.44 moles of hexafluoroacetylacetone (Hfac) are added to the vessel at a rate of 5 ml Hfac per minute.

(f) After the material in step E has been added, the reaction is stirred overnight in an anaerobic environment.

(g) When the reaction has been allowed to stir for 24 hours, the product is recovered by filtering through a 0.2 micron filter and stored in an anaerobic environment.

(h) Further purification means are then employed to remove impurities, excess unreacted starting materials and water, including using chemisorption through silica and/or alumina gels; molecular sieves; ion exchange resins, activated carbon; vacuum and/or sparge stripping; reverse osmosis; membrane separation; and water/liquid separation techniques.

EXAMPLE 1

Synthesis of Copper(+1)(hfac)(2-methyl 3-buten-2-ol)

Runs were carried out to synthesize monovalent copper (+1)(hfac)(2-methyl 3-buten-2-ol) using the above general synthesis above using 2-methyl-3-buten-2-ol as the ligand in step (c). The resulting solution was then filtered and purified in a conventional manner to remove the unreacted materials and any copper (+2) species that might be present and the water of condensation that is formed in the reaction mixture. The final product was identified by x-ray crystallography. Yield: 95%.

EXAMPLE 2

Chemical Vapor Deposition (CVD) of copper metal Using Copper(+1)(hfac)(2-methy-3-buten-2-ol)

CVD copper using copper(+1)(hfac)(2-methyl-3-buten-2-ol) (Sample 1) was carried out in conventional manner on a tantalum surface. Subsequent to the deposition the metallic copper films were evaluated for adhesion and resistivity. Comparisons were made to the prior art copper(+1) (hexafluoroacetylacetonate)trimethylvinylsilane complex (Sample 2) as the standard.

Cu(hfac) (2-methyl-3-buten-2-ol) Deposition process parameters:

| | | |
|---|---|---|
| Chamber Temperature: | 180° C. | typical range: 150–225° C. |
| Chamber pressure: | 1.5 Torr | typical range: 0.2–5 Torr |
| Precursors flow rate: | 0.1–0.2 ml/min | typical range: 0.05–2 ml/min |
| Inert carrier (He) flow rate: | 210 sccm | typical range: 0–1000 sccm |

Anneal temp: 400° C., 30 minutes in forming gas at ambient pressure

Sample 1 resistivity before anneal: 13–15 uohm-cm

Sample 1 resistivity after anneal: 2.0–3.0

Sample 1 adhesion before anneal: 3 (relative scale=1 to 4)

Sample 1 adhesion after anneal: 4 (relative scale=1 to 4)

Sample 2 Cu(hfac)TMVS standard: 1 before anneal, 2–3 after anneal (relative scale 1–4).

In summary the synthesis and manufacture of new and improved class of copper(+1)(β-diketonate)(L) complex products allows for the deposition of highly conducting, thin films of copper on metallic surfaces such as Ta, TaN, Ir, Rh, Ru, Pt, Ti, TiN and W, notwithstanding other metals. Copper deposition of films with good adhesion and low stress can be accomplished after annealing for 30 minutes at 400° C. in forming gas (5% $H_2$ in $N_2$), to give a resistivity of approximately 2 microohms-cm (pohm-cm).

What is claimed is:

1. A monovalent copper(+1)(β-diketonate)(L) or monovalent copper(+1)(β-ketoiminate)(L) complex represented by the formula:

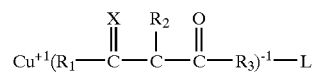

wherein X represents O or $NR_9$ wherein $R_1$ and $R_3$ are each independently, selected from the group consisting of $C_{1-8}$ alkyl, $C_{1-8}$ fluoroalkyl, aryl, $C_{1-8}$ alkoxy, and $C_{1-8}$ alkyl ethers and $R_2$ is H, $C_{1-8}$ alkyl, $C_{1-8}$ alkoxy, and halogen, $R_9$ is $C_{1-8}$ alkyl, $C_{1-8}$ fluoroalkyl, phenyl, alkylpheny, trialkylsilyl, and L represents a ligand having the structure:

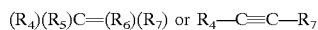

wherein $R_4$ is selected from the group consisting of $C_{1-8}$ alkanol, $C_{1-8}$ alkoxyalkanol, $C_{1-8}$ unsaturated alkoxyalkanol, trialkylsilanol, $C_{1-8}$ alkylamine, phenylamine; $R_5$, $R_6$, and $R_7$ are selected from the group consisting of H, $C_{1-8}$ alkyl, triakylsilyl, alkoxy or phenyl.

2. The complex of claim 1 wherein X is O.

3. The complex of claim 2 wherein $R_1$ and $R_3$ are selected from the group consisting of $C_{1-3}$ alkyl and $C_{1-3}$ fluoroalkyl.

4. The complex of claim 3 wherein $R_2$ is H.

5. The complex of claim 4 wherein L is represented by the formula:

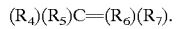

6. The complex of claim 5 wherein $R_4$ is $(CH_3)_2COH$.

7. The complex of claim 6 wherein $R_5$, $R_6$, and $R_7$ are H.

8. The complex of claim 7 wherein $R_1$ and $R_3$ are $CF_3$.

9. The complex of claim 2 wherein β-diketonate portion of the compound is derived from a β-diketone selected from the group consisting of 1,1,1,5,5,5-hexafluoro-2,4-pentanedione; 4-(2,2,2-trifluoroethyl)imino-1,1,1,5,5,5-hexafluoro-2-pentanone; 5-(2,2,2-trifluoroethyl)imino-1,1,1,2,2,6,6,6-octafluoro-3-hexanone, and 6-(2,2,2-trifluoroethyl)imino-1,1,1,2,2,3,3,7,7,7,-decafluoro-4-heptanone.

10. The complex of claim 4 wherein L is represented by the formula:

$$R_4\text{—}C\equiv C\text{—}R_7.$$

11. The complex of claim 10 wherein $R_4$ is $CH_2OH$.

12. The complex of claim 11 wherein $R_7$ is H.

13. The complex of claim 12 wherein $R_1$ and $R_3$ are $CF_3$.

14. The complex of claim 9 wherein the β-diketonate portion is derived from 1,1,1,5,5,5-hexafluoro-2,4-pentanedione and the ligand L is derived from 2-methyl 3-buten-2-ol.

15. The complex of claim 1 wherein X is $NR_9$.

16. The complex of claim 15 wherein $R_1$ and $R_3$ are selected from the group consisting of $C_{1-3}$ alkyl and $C_{1-3}$ fluoroalkyl and $R_2$ is H.

17. The complex of claim 16 wherein $R_9$ is $C_{1-3}$ fluoroalkyl.

18. The complex of claim 17 wherein L is represented by the formula:

$$(R_4)(R_5)C\!=\!(R_6)(R_7).$$

19. The complex of claim 18 wherein $R_4$ is $(CH_3)_2COH$ and $R_5$, $R_6$, and $R_7$ are H.

20. In a process for the chemical vapor deposition of copper metal on metallic substrates or electrically conducting portions of a substrate using organometallic copper compounds, the improvement which comprises using the monovalent copper complex of claim 1 as the organometallic copper compound.

* * * * *